United States Patent [19]

Liu

[11] Patent Number: 4,927,976

[45] Date of Patent: May 22, 1990

[54] PROCESS FOR PREPARING 2,3-BIS(HYDROXYETHOXYMETHYL) BICYCLO [2,2,1] HEPTANE AND POLYESTER THEREWITH

[75] Inventor: Kou-Chang Liu, Wayne, N.J.

[73] Assignee: GAF Chemicals Corporation, Wayne, N.J.

[21] Appl. No.: 402,370

[22] Filed: Sep. 5, 1989

[51] Int. Cl.$^5$ .............................................. C07C 43/02
[52] U.S. Cl. .................................... 568/665; 568/670
[58] Field of Search .............................. 568/665, 670

[56] References Cited

U.S. PATENT DOCUMENTS 3,492,330  1/1970  Trecker et al. .................... 260/453

FOREIGN PATENT DOCUMENTS 857937  10/1940  France .

OTHER PUBLICATIONS

Birch, *J. Org. Chem.*, vol. 21, pp. 970≅975 (1956).

*Primary Examiner*—Bruce Gray
*Attorney, Agent, or Firm*—Walter Katz; Marilyn J. Maue; Joshua J. Ward

[57] ABSTRACT

What is provided herein is a process for preparing 2,3-bis(hydroxyethoxymethyl) bicyclo [2,2,1] heptane (BHEMBCH). In accordance with another feature of the invention, a polyester which is chain extended with BHEMBCH also is provided herein.

1 Claim, No Drawings

PROCESS FOR PREPARING 2,3-BIS(HYDROXYETHOXYMETHYL) BICYCLO [2,2,1] HEPTANE AND POLYESTER THEREWITH

CROSS-REFERENCE TO RELATED PATENT APPLICATIONS

An improved FDN-1433, Ser. No. 07/402,577, filed 09/05/89, describes an improved process for the preparation of 2,3-bis(hydroxymethyl) bicyclo [2,2,1] heptane, and a polyester made therewith.

BACKGROUND OF THE INVENTION

1. Field of the Invention

This invention relates to chain extenders for polyester elastomers, and, more particularly, to a process for preparing 2,3-bis(hydroxyethoxymethyl) bicyclo [2,2,1] heptane (BHEMBCH) for use in the preparation of polyester elastomers therewith.

2. Description of the Prior Art 2,3-Bis(hydroxymethyl) bicyclo [2,2,1] heptane (BHMBCH) has been described in the literature. See Birch et al., J. of Org. Chem. 21, 970–974 (1956). The Birch synthesis involved three separate steps, namely, (1) a Diels-Alder condensation of cyclopentadiene and maleic anhydride to form an unsaturated anhydride; (2) reduction of the anhydride with lithium aluminum hydride to produce an unsaturated diol; and (3) hydrogenation over a palladium catalyst to provide the saturated diol. However, in the process, a considerable quantity of undesirable by-products were obtained during step (2), and, accordingly, four crystallizations of the crude unsaturated diol were required before the hydrogenation step (3) could be carried out effectively.

French Patent No. 857,937 described the preparation and isolation of the unsaturated diol intermediate only. The process comprised reaction between cyclopentadiene and 1,4-butenediol in dioxane solvent. However, dioxane is extremely toxic and difficult to remove completely from the reaction product.

U.S. Pat. No. 3,492,330 disclosed reactions of bridged-ring olefins, including the unsaturated diol with functional alkanes. The patentee said the unsaturated diol could be prepared from cyclopentadiene and 1,4-butenediol by a classical Diels-Alder reaction.

The aforementioned copending patent application describes an improved process over the stated prior art for making BHMBCH and a polyester product made therefrom. In this invention, a more advantageous chain extender (BHEMBCH) for making polyesters is prepared for use in the synthesis of polyesters.

SUMMARY OF THE INVENTION

What is provided herein is a process for preparing 2,3-bis(hydroxyethoxymethyl) bicyclo [2,2,1] heptane (BHEMBCH). In accordance with another feature of the invention, a polyester which is chain extended with BHEMBCH also is provided herein.

DETAILED DESCRIPTION OF THE INVENTION

The synthesis of 2,3-bis(hydroxyethoxymethyl) bicyclo [2,2,1] heptane [BHEMBCH] is as follows:

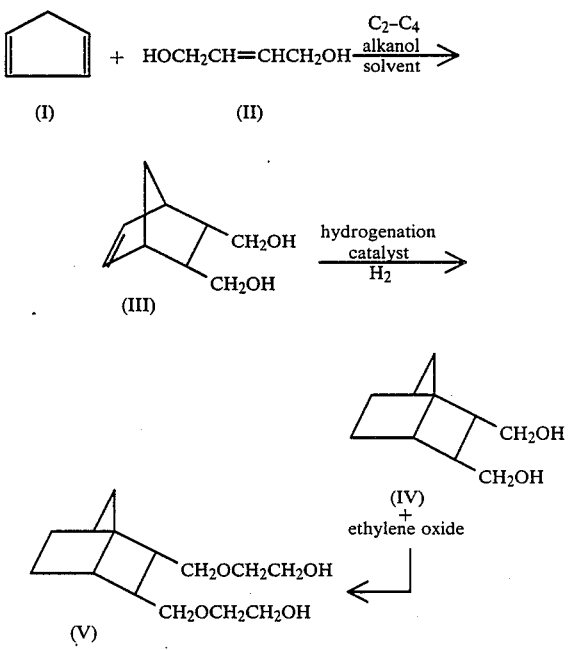

Accordingly, cyclopentadiene (I) and 2-butene-1,4-diol (II), in a molar ratio of about 1:1 to 2:1, respectively, are heated at a temperature of about 140° to 200° C. for 5 to 20 hours, in a $C_2$–$C_4$ straight or branched chain alcohol solvent, e.g. ethanol, at a solvent level of about 20 to 200% by weight of the reaction mixture, to produce the unsaturated diol intermediate (III) in high yield.

In the same pot and alcohol solvent, (III) is hydrogenated at a temperature of about 50° to 200° C. for 1 to 20 hours with a hydrogenation catalyst to produce the saturated diol (III). Generally, the catalyst comprises about 0.05 to 5% by weight of (III). Suitable hydrogenation catalysts include palladium, platinum, rhodium, and the like, which may be supported or unsupported. Suitable supports include charcoal, calcium carbonate, etc. The overall yield of (IV) is at least 50%.

Then (IV) is reacted with ethylene oxide under basic conditions at about 100°–150° C. under nitrogen and a pressure of about 15–40 psig to produce the desired ethoxylated diol (V).

The polymerization reaction of (V) with terephthalic acid or isophthalic acid provides chain extended polyesters which are effective engineering plastics, particularly at elevated use temperatures.

The terms "terephthalic acid" and "isophthalic acid" as used herein are intended to include the condensation polymerization equivalent of such acids, i.e. their esters or ester-forming derivatives such as acid chlorides and anhydrides, or other derivatives which behave substantially like such acids in a polymerization reaction with a glycol. Dimethyl terephthalate and dimethyl isophthalate are, for instance, suitable starting materials for the polyester polymers of the invention.

The invention will now be described by reference to the following examples.

EXAMPLE 1

Preparation of 2,3-Bis(Hydroxymethyl) Bicyclo [2,2,1] Heptane (BCHMCH)

Cyclopentadiene (150 g., 2.28 moles), 2-butene-1,4-diol (150 g., 1.7 moles) and ethanol (300 g.) were charged into a 1-liter stainless steel autoclave. The autoclave was purged three times with nitrogen at 100 psig and then heated to 175° C. for 10 hours. After being cooled to room temperature, 3 g. of 5% Pd on charcoal was added to the mixture. The mixture was purged two times with nitrogen, heated to 170° C. and hydrogenated at 100 psig. The hydrogenation was completed in 7 hours.

The crude product was filtered to remove the catalyst and rotoevaporated to remove ethanol. The semisolid material obtained was distilled at 0.3–0.5 mm of Hg. The desired product comprised a forecut of 32.7 g. of material and a center cut of 150.1 g. of a pale yellow solid (m.p. 52°–56° C.). The solid was recrystallized from 100 ml toluene-50 ml hexane to give 124 g. of white solid; m.p. 57°–60° C., which was identified by NMR as the title compound.

EXAMPLE 2

Preparation of 2,3-Bis (2-Hydroxyethoxymethyl) Bicyclo [2,2,1] Heptane (BHEMBCH)

2,3-Bis(hydroxymethyl)-bicyclo [2,2,1] heptane (BCHMCH) (656.6 g.) and sodium hydroxide (0.66 g) were charged into a one gallon stainless steel autoclave. The mixture was heated to 70° C. and purged three times with nitrogen. The autoclave was pumped at 20 mm Hg and 110° C. for one-half hour to remove water.

The solution was then brought to 155° C. and ethylene oxide (369.6 g,. 8.4 moles) was added at 30 psig in 3 hours. After cooling to room temperature, the autoclave was purged two times with nitrogen. Crude BHEMBCH was obtained as a pale yellow oil. Molecular distillation of 360 g of the crude oil at 160° C. and 0.1 mm Hg afforded a center cut of 287 g of BHEMBCH as a colorless viscous liquid.

EXAMPLE 3

Preparation of Polyester of Invention

A mixture of dimethyl terephthalate (97.1 g), BHEMBCH (146.4 g) and tetraisopropyl titanate (0.12 g) is heated in a 500 ml resin kettle at 150° C. and 10 mm Hg. The methanol generated is continuously removed from the system. After 2 hours, the vacuum is further reduced to 0.2 mm Hg and the temperature is increased to 240° C. to remove excess BHEMBCH. Nitrogen is introduced into the system during this period. The polymeric reaction product then is discharged, and characterized by IR and NMR to be the desired polyester shown below:

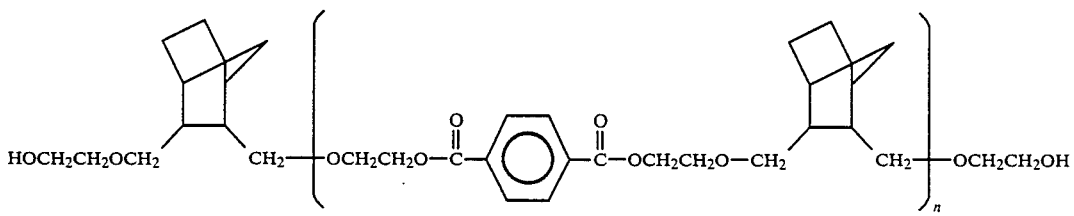

where n is 5 to 5000.

While the invention has been described with particular reference to certain embodiments thereof, it will be understood that changes and modifications may be made which are within the skill of the art. Accordingly, it is intended to be limited by the appended claims only, in which:

What is claimed is:

1. The compound 2,3-bis(hydroxyethoxymethyl) bicyclo [22,1] heptane.

* * * * *